June 2, 1959 C. J. DYKSTRA Plant Pat. 1,838
APPLE TREE
Filed March 7, 1958
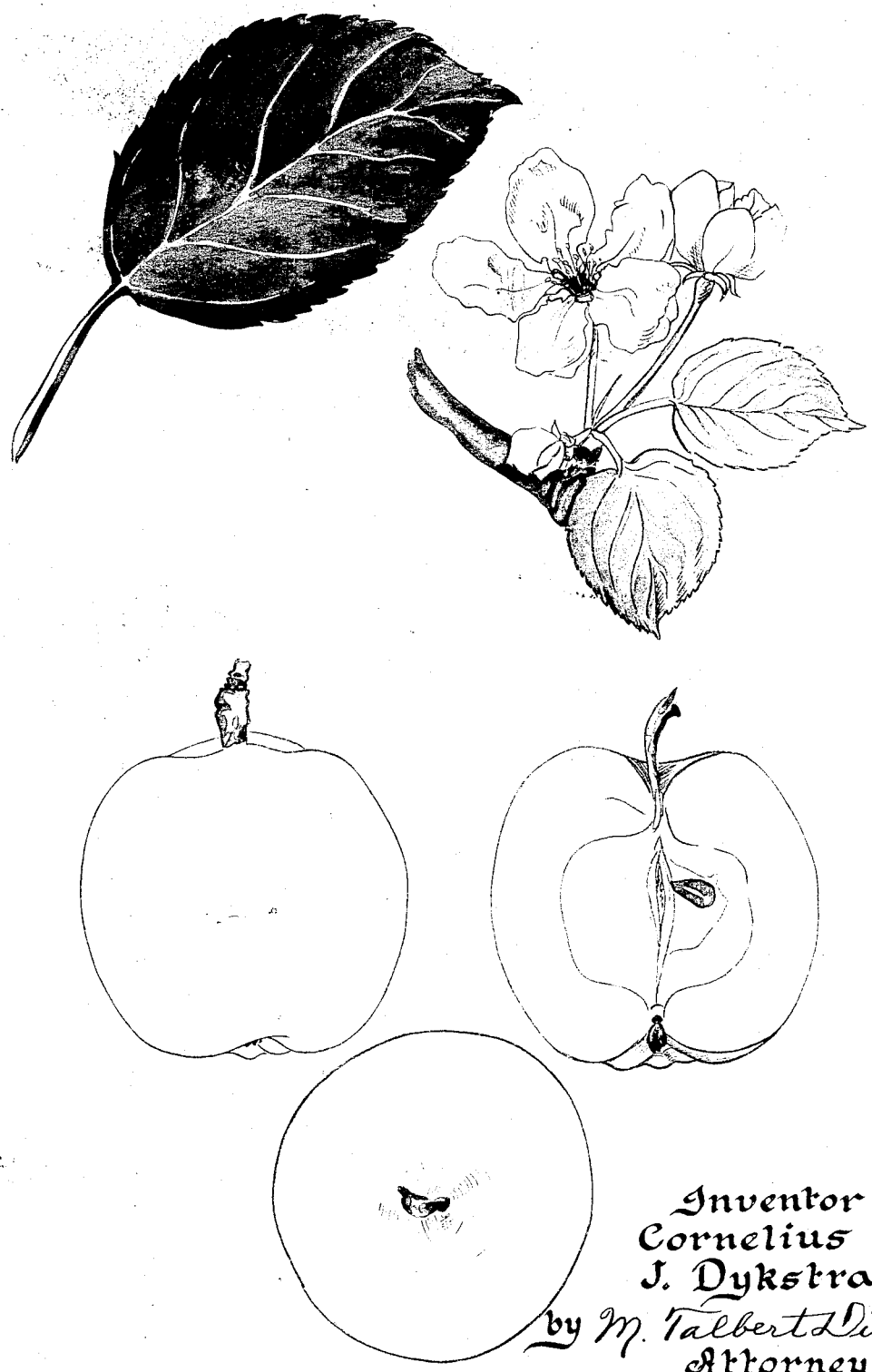
Inventor
Cornelius
J. Dykstra
by M. Talbert Dick
Attorney United States Patent Office Plant Pat. 1,838
Patented June 2, 1959

1,838

APPLE TREE

Cornelius J. Dykstra, Des Moines, Iowa

Application March 7, 1958, Serial No. 719,984

1 Claim. (Cl. 47—62)

My invention relates to a new and distinct variety of apple tree and its apples, the novel characteristics of which particularly reside in its fruit firmness, superb keeping qualities making for a long marketing season, color, a deeper axial dimension, a resistance to insects and disease, a tree that has an excellent resistance to high and low temperature changes, and evenly produces apples along the longitudinal lengths of its branches.

The original trees, in the arrangement of a small groupment, were the result of apple seeds and pulp from cider making and which I discarded on the ground in my orchard located in Des Moines, in Polk County, Iowa. I permitted the three strongest sprouts of the group to live, but they did not particularly signify any new and unique character to me until in the spring of 1941. The reason my attention was directed to these new trees was the fact that they successfully survived the killing winter storm of November 11, 1940. One of these contemporaries of the group was cut in two in 1956 and showed ring growth proving the seed planting in 1936, or the year the seed and pulp were thrown on the orchard ground.

Parentage is unknown unless it can be assumed from its somewhat marked resemblance to Yellow Transparent (not patented) that the Yellow Transparent is one of the parents. If so, it would likely be the pollen parent as I had none of that variety in my orchard at the time, but it was available from neighbors' trees. After observing that I had an apple tree and apples of different characteristics than that of other apple trees and their apples, I asexually reproduced this apple tree in my orchard at Des Moines, Polk County, Iowa. The manner of asexually reproducing this apple tree was in top working by cleft grafting cuttings, on an existing apple root variety such as a seedling.

*Tree*

The tree is of medium size, clean, unblemished and hardy in appearance. It makes a normal vigorous growth without being excessive. The branching is average to open and can be easily trimmed to produce the desired branching.

To date it is an annual bearing tree with fruit almost always spaced apart evenly on the branch. This is a distinct characteristic of the tree and fruit.

*Leaves*

The leaves are similar to the leaves of most all apple trees. They are of normal size and have saw-toothed peripheral edges. The mature leaves are of the usual glossy dark green color and the young leaves are glossy but of a much lighter green color.

*Blooms*

The blossoms are similar to most all apple tree blooms. The buds are white and pink, but after opening they are shell white with traces of pale pink. The pale pink area is quite often in the outer area of the petal. The blooming period is from May first to May ninth.

*Temperatures*

Grows well in warm or hot weather and has never been frozen back. Its resistance to freezing is particularly apparent since the area where it is growing is subject to severe and extreme low temperatures in the winter.

*Dry and wet seasons*

Has never shown any deterioration either during extremely dry or wet years.

*Fruit*

The appearance of the fruit differs from the Yellow Transparent apples in that the color is more of a greener tinge, i.e., the skin of the fruit has a yellow greenish appearance during the early marketing period. The skin of the fruit is clear, hard and glossy, which adds to its effectiveness. If the fruit is left on the tree past the normal marketing period, it becomes more of a golden color and loses a part of its green tinge. At final marketing maturity the fruit has an added color in the form of one or more short pink stripes starting from near the stem end. The more exposure to the sun, the more pronounced will be these pink stripes, resulting in the appearance of a pink blush or patch.

*Fruit marketing period*

The apples may be picked at the beginning of the season at substantially the same time as the Yellow Transparent apples are picked. However, the fruit has a firmness and a solidity that the picking season is extended at least three weeks after the end of the picking season for the common Yellow Transparent varieties. This makes for an extended marketing season of at least five weeks. Inasmuch as the fruit has a firm and hard character, it does not bruise easily and it keeps well both off the tree and on the tree. In cold storage the apples can be kept for months.

*Flavor of the fruit*

The flavor of the fruit differs from that of the Yellow Transparent varieties by having a sharper and more tart flavor. The flavor is quite distinctive and the fruit is excellent for making apple sauce. Also the flesh of the apple is quite crisp and juicy.

*Size of the fruit*

At all stages of growth and final size, the fruit differs from the Yellow Transparent varieties by having a greater axial dimension. The average apple has a radial diameter of approximately two and three-fourths inches, and a longitudinal diameter of approximately two and five-eighths inches.

*Resistance to diseases*

The fruit is definitely resistant to diseases and particularly to apple scab. In two successive years, i.e., 1956 and 1957, an adjoining McIntosh (not patented) apple branches extended and intermingled with the branches of my apple tree. The McIntosh apple tree was so badly infected with apple scab that the fruit was not salable. My fruit, however, and the leaves of the trees remained clear of the apple scab and not a particle of the scab was evident on the apples although the trees received the same spraying and treating schedule. The leaves of my trees were substantially clear and unaffected.

*Fruit structure*

Representative fruit shows twelve perfect seeds and three imperfect seeds. Usually the fruit is of five cells.

I claim:

A new and distinct variety of apple tree and fruit characterized as to novelty in fruit firmness, superb keeping qualities, extended marketing season, a deep axial dimension, resistance to disease, a fruit that is of greenish yellow color having a short pink stripe or stripes from its stem end as it matures, and a tree that has excellent resistance to high and low temperatures and produces apples substantially evenly spaced apart along the longitudinal length of its branches.

References Cited in the file of this patent

UNITED STATES PATENTS

| | | |
|---|---|---|
| P.P. 1,470 | Barkley | Apr. 17, 1956 |
| P.P. 1,550 | Law | Jan. 8, 1957 |
| P.P. 1,565 | Bisbee | Feb. 12, 1957 |